United States Patent [19]
Winograd et al.

[11] Patent Number: 5,272,338
[45] Date of Patent: Dec. 21, 1993

[54] MOLECULAR IMAGING SYSTEM

[75] Inventors: Nicholas Winograd; Stephen J. Benkovic, both of State College, Pa.

[73] Assignee: The Pennsylvania Research Corporation, University Park, Pa.

[21] Appl. No.: 887,201

[22] Filed: May 21, 1992

[51] Int. Cl.$^5$ ............................................. H01J 37/252
[52] U.S. Cl. .................................. 250/309; 250/423 P
[58] Field of Search .................... 250/309, 288, 423 P, 250/251

[56] References Cited

U.S. PATENT DOCUMENTS

| | | | |
|---|---|---|---|
| 3,987,302 | 10/1976 | Hurst et al. | 250/283 |
| 4,426,576 | 1/1984 | Hurst et al. | 250/283 |
| 4,442,354 | 4/1984 | Hurst et al. | 250/281 |
| 4,633,084 | 12/1986 | Gruen et al. | 250/423 P |
| 4,658,135 | 4/1987 | Allman et al. | 250/283 |
| 4,733,073 | 3/1988 | Becker et al. | 250/288 |
| 4,874,947 | 10/1989 | Ward et al. | 250/309 |
| 4,939,360 | 7/1990 | Sakai | 250/251 |
| 5,065,018 | 11/1991 | Bechtold et al. | 250/423 P |
| 5,105,082 | 4/1992 | Maruo et al. | 250/309 |
| 5,148,027 | 9/1992 | Umemura et al. | 250/309 |

Primary Examiner—Bruce C. Anderson
Attorney, Agent, or Firm—Thomas J. Monahan

[57] ABSTRACT

An ion-beam based system enables quantitative analysis and visualization of a sample with atomic and molecular specificity. The system comprises a liquid metal ion source that directs a tightly focused beam of ions at the sample, the beam having an ion density that is insufficient to materially change the surface properties of the sample. A controller connected to the liquid metal ion source gates on the ion beam for a period of time that is sufficient to enable the ion source to achieve a tight focus of the beam at the sample and for further scanning the ion beam across the sample. A laser beam is positioned over the sample and has a wavelength that resonantly ionizes components of the sample that are liberated by action of the scanned ion beam. A detector measures the liberated ionized components and is connected to a display system that provides an image of the distribution of the species on surface of the sample.

6 Claims, 4 Drawing Sheets

MOLECULAR IMAGING SYSTEM

FIELD OF THE INVENTION

This invention relates to high sensitivity mass spectroscopy and, more particularly, to a system for imaging atoms and molecules employing mass spectroscopic techniques.

BACKGROUND OF THE ART

It has now become feasible for cellular biochemists to determine the chemical constituents of a single cell. This breakthrough has been achieved as a result of the discovery of new chemical separation and detection methodologies which are sensitive at the femtomole level and below. Moreover, it is now possible to manipulate a wide variety of cells and even to insert electrochemical probes inside the cores of these materials for in-vivo studies. These tools allow elucidation of the function of single cells, as contrasted to assemblies of cells and are driving new approaches to an understanding of the mechanisms of cellular functions.

Subcellular localization and imaging of molecules can provide a further dimension for monitoring of chemical processes. The imaging of such molecules is extremely difficult. Most biological cells have diameters in the range of 1-10 microns, although a few types of neurons are known to be as large as 500 microns. To provide a reasonable spatial image of a molecule, there should be at least 10 picture elements (pixels) along each dimension of the cell. Submicron molecular imaging requires both spatial resolution below the resolving power of optical systems and molecular specificity to enable detection of species of different atomic weights.

There have been a number of methods developed in order to approach sub-micron imaging. The most sensitive methods involve the detection of specific types of atoms which may also act as tags for a target molecule. X-ray microanalysis, electron-energy-loss spectroscopy, Auger electron spectroscopy and secondary ion mass spectrometry (SIMS) have been pursued in this regard.

For some time it has been known that molecular ions may be desorbed from surfaces bombarded by heavy keV particles. This procedure is known as secondary ion mass spectroscopy (SIMS) and involves the use of an ion source to bombard the sample and a subsequent measurement of the mass of desorbed particles. In its dynamic form, SIMS employs a high energy ion beam that erodes the sample but provides a high level of desorbed particles for detection purposes. In another form, known as "static" SIMS, a considerably smaller dose of incident ions is employed having a beam density sufficiently low so as to avoid sample surface damage (usually less than $10^{13}$ ions per square centimeter). Static SIMS has the advantage that mass spectra of surfaces can be obtained but suffers the disadvantage that only few desorbed particles are available for measurement.

Recently, a new SIMS technique has been developed that is referred to as "time-of-flight" SIMS. This method employs a pulsed ion gun and can be operated in the static SIMS mode because of its high collection efficiency. The time-of-flight of the desorbed species allows derivation of the species' mass. Imaging has been performed in a time-of-flight SIMS system, but submicron spatial resolution for molecular species has not been feasible since there are not sufficient desorbed ions for measurement purposes.

Another spectrometry method has been reported that overcomes some of the sensitivity drawbacks of prior art static SIMS techniques. That procedure is termed "sputter initiated resonance ionization spectrometry" and is further described in U.S. Pat. Nos. 3,987,302; 4,426,576; 4,442,354 and 4,658,135 to Hurst et al. The Hurst et al. system bombards a sample with ions to create a cloud of secondary ions and neutral particles. The cloud is irradiated with a laser pulse that is tuned to ionize the neutral particle species by means of multiphoton resonance ionization. Then, the mass of the ionized particles is determined by a time of flight spectrometry method. The laser irradiation enables the creation of a substantially greater quantity of ionized species for measurement purposes, but requires a 1-2 millimeter diameter focused laser spot. If a more tightly focused spot is employed, much fewer ions are generated, even with the laser assisted ionization.

Still another mass spectrometry method is described by Becker et al in U.S. Pat. No. 4,733,073. In the Becker et al system, a highly focussed laser beam is employed to ionize particles from a sample surface. The laser beam is not tuned to achieve resonance ionization, but achieves ionization action through the beam's high power. Due to the tight focus of the beams, however, the beam interacts with just a small portion of the cloud of particles over the sample's surface, and particle sensitivity suffers.

Concomitant with the development of static SIMS has been the discovery that a liquid metal ion gun (LMIG) can be employed to focus ion beams to a spot size as small as 200 Angstroms in diameter. The LMIG is characterized by an extremely high current density that enables high sensitivity but introduces a number of artifacts due to beam damage when operated in the dynamic mode. The LMIG has recently been commercialized and incorporated into a high transmission reflectron time-of-flight analyzer. By taking advantage of its high detection efficiency and by operating this instrument in the static mode, others have been able to image tripeptides from a conducting substrate with spatial resolutions approaching one micron.

A traditional problem with SIMS and other spectrometry systems that rely upon ion bombardment is the presence of large matrix ionization effects. Both the ionization potential of the target molecule, as well as the electronic properties of the matrix surrounding the molecule exponentially influence the probability of ion formation. Furthermore, the number of ions produced during desorption is generally several orders of magnitude smaller than the number of neutral species. Ionization effects have thus created severe problems with such spectrometry methods.

Accordingly, it is an object of this invention to provide an atomic and molecular imaging system that exhibits resolution levels in the hundreds of Angstroms.

It is another object of this invention to provide an improved resonance ionization spectrometry system for imaging the presence of molecular species across a surface.

It is still another object of this invention to provide a molecular level imaging system that employs a highly focused ion beam that does not materially change the surface properties of the sample.

SUMMARY OF THE INVENTION

An ion-beam based system enables quantitative analysis and visualization of a sample with atomic and molecular specificity. The system comprises a liquid metal ion source that directs a tightly focused beam of ions at the sample, the beam having an ion density that is insufficient to materially change the surface properties of the sample. A controller connected to the liquid metal ion source gates on the ion beam for a period of time that is sufficient to enable the ion source to achieve a tight focus of the beam at the sample and for further scanning the ion beam across the sample. A laser beam is positioned over the sample and has a wavelength that resonantly ionizes components of the sample that are liberated by action of the scanned ion beam. A detector measures the liberated ionized components and is connected to a display system that provides an image of the distribution of the species on surface of the sample.

DETAILED DESCRIPTION OF THE INVENTION

Figure 1:
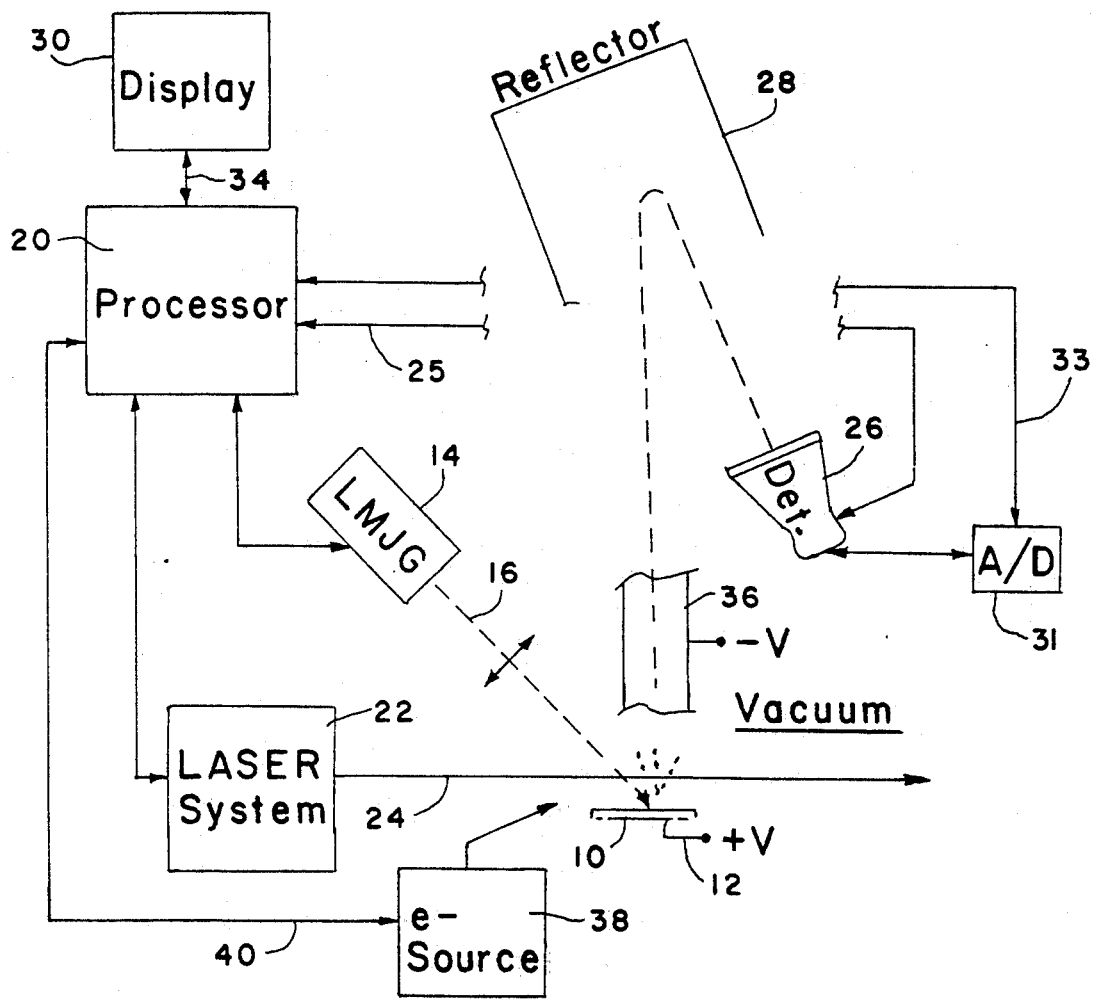
FIG. 1 is a block diagram of a system that incorporates the invention.

Referring to FIG. 1, a conductive sample substrate 10 has coated on its upper surface a molecular sample to be visualized and analyzed (not shown). Substrate 10 is biased by a high positive potential 12. A liquid metal ion gun 14 directs a pulsed ion beam 16 to a highly focused point on substrate 10, which ion beam causes atomic and molecular particles to desorb from the surface of the sample. Ion beam 16 is scanned across the surface of substrate 10 in the known raster scan manner. A set of accelerating plates 36 are positioned over substrate 10 and are heavily negatively biased to accelerate ionic species emanating from above substrate 10 in the direction of reflector 18. Control of LMIG 14 derives from processor 20 which also controls operation of the other major components of the system. Those systems include a laser system 22 which directs a laser beam 24 across the surface of substrate 10 at such a height that it intersects the cloud of desorbed particles from the sample on substrate 10. Additionally, controller 20 is connected via line 25 to a microchannel platedetector 26 and provides gating signals thereto to enable it to detect ions directed at it from a reflector 28. The output from microchannel platedetector 26 is applied through an analog-to-digital converter 31 and line 33 to processor 20. A display unit 30 is connected to processor 20 and derives its timing, image input and sweep signals therefrom.

The imaging system of FIG. 1 is arranged to image biological species that are nonconductive in nature. Such species will tend to attain a positive charge during the operation of LMIG 14 which charge will cause interference with the operation of the system. An electron source 38 is energized during intervals between the gating of LMIG 14, to inject electrons into the region of the sample for neutralization purposes. The operation of electron source 38 is controlled by signals on line 40 from controller 20.

As will be hereinafter understood, the system of FIG. 1 employs time-of-flight measurement techniques previously employed in time-of-flight SIMS systems. In any time-of-flight configuration, the presence of a well-defined start pulse is critical. To obtain reasonable mass resolution in prior art time-of-flight SIMS systems, the incident ion pulse is used as the start pulse and is typically five nanoseconds in time width. For a 100 pico second ion pulse, such a narrow gating pulse means that each ion pulse contains approximately three ions. Furthermore, it proves extremely difficult to focus a five nanosecond ion pulse to a size of less than 2000 Angstroms due to field artifacts associated with the pulsing mechanism.

Those field artifacts result from the fact that the gating structure in the LMIG utilizes a deflection signal to move the ion beam into and out of an aperture, with the beam being gated "on" when positioned in the aperture. With a five nanosecond gating, the beam spends a considerable portion of its "on" time in moving both into and out of the aperture. As the beam is swept from the edge of the aperture to its center, the beam creates a highly varying ion flux on the sample. Because of the beam's fine focus, the short duration of the ion pulse, and the rapidly changing ion flux, to focus the beam to a spot of less than 2000 Angstroms is therefore largely unattainable. This problem has been overcome in the system of FIG. 1 as the laser pulse is employed as the start pulse rather than the ion pulse.

Prior to discussing the detailed operation of FIG. 1, its major components will be further detailed. LMIG 14 functions by field ion emission of a liquid metal which is coated at a tungsten tip. A large extraction potential ionizes the liquid metal and the ions, once desorbed from the very small tip, can be refocused to an area as small as 200 Angstroms. LMIGs are available commercially and one such supplier is F.E.I. Co., 19,500 N.W. Gibbs Drive, Suite 100 Beaverton, Oreg. 97006-6907. The FEI LMIG source is capable of producing very stable beams of gallium, indium or tin with a kinetic energy range of 1 to 30 keeV.

As indicated above, the start pulse is the pulse from controller 20 that causes laser system 22 to produce laser beam 24. It has been calculated that for a laser beam of 5 millimeters in diameter, positioned one millimeter above the target on substrate 10, that 60% of the desorbed flux overlaps the laser pulse if a 3 microsecond incident ion pulse is used. The use of a longer ion pulse produces a number of significant advantages. First, each 100 pico amp pulse contains 2000 ions rather than just 3 (i.e., a five nanosecond pulse). Moreover, LMIG 14 and its internal components are able to focus a longer duration ion pulse to a beam size, at the sample, on the order of 500 Angstroms. While a 3 microsecond ion pulse has been used in certain experiments, ion pulses in the 100-300 nanosecond range can be similarly focused and still provide sufficient ion fluxes.

Figure 2:
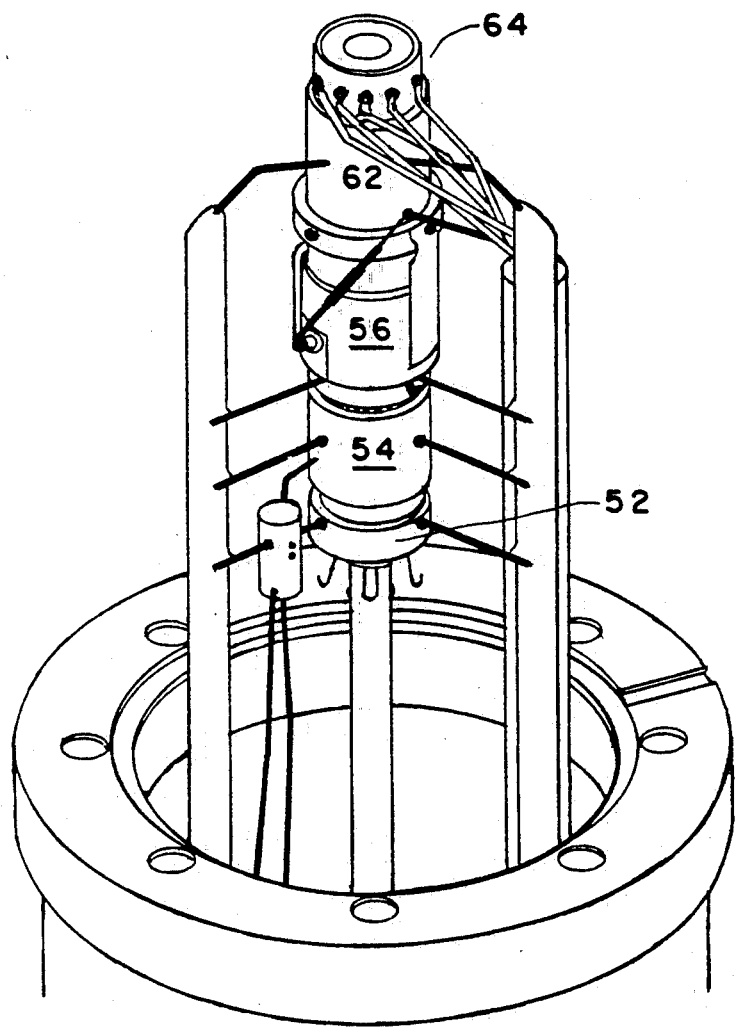
FIG. 2 is a perspective view of a liquid metal ion gun (LMIG) employed in the invention.
Figure 3:
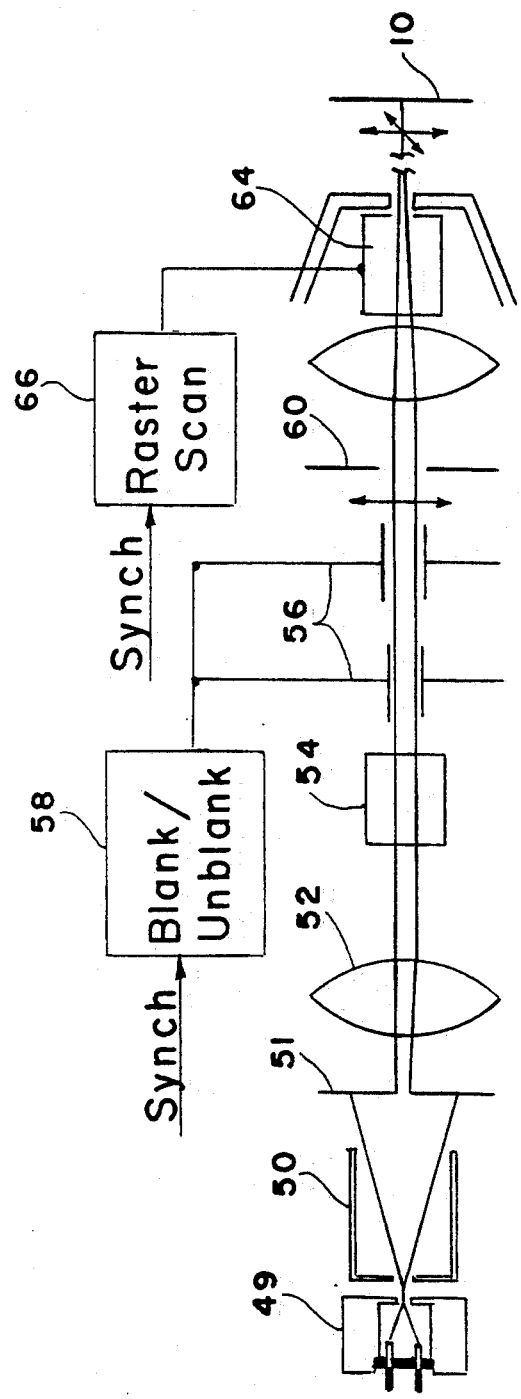
FIG. 3 is a schematic of the liquid metal ion gun of FIG. 2.

In FIG. 2, a perspective of LMIG 14 is shown illustrating its major components and its schematic is shown in FIG. 3. As shown in FIG. 3, a liquid gallium source 49 causes a flux of ions to enter into extractor cap 50 and pass through fixed aperture 51. The ion flux experiences a first lens element 52 and then an intermediate octopole focusing element 54. Next, the partially focused ion beam enters between a plurality of beam blanking plates 56, to which beam control signals are applied from blanking/unblanking circuit 58. A beam blanking aperture 60 is positioned immediately after beam blanking plates 58 and acts as the on-off control for the ion beam.

To blank the ion beam, a potential is applied to plates 56 by blanking/unblanking circuit 58 so as to cause the ion beam to deflect from the opening in aperture plate 60. As a result, the ion beam is "blanked" and does not pass through the remaining focus elements of the system. As above indicated, the duration of the blanking signals generated by blanking/unblanking circuit 58 is sufficiently long to prevent the pulsed ion beam from exhibiting field artifacts caused by its traversal across beam blanking aperture plate 60.

When the blanking potentials are removed from plates 56, the ion beam returns to its central location and passes on to a second lens arrangement 62 that includes a second octopole focusing element 64. In addition to appropriate focusing voltages, a scan potential is applied to octopole 64 from raster scan circuit 66 so as to enable deflection of the ion beam in a raster fashion across substrate 10.

Laser system 22 must satisfy several criteria so as to be able to initiate multiphoton resonance ionization with high efficiency. Preferably, laser system 22 should be tunable from the UV to the near IR and must be pulsed in order to achieve a high peak power. High repetition rates are desirable to avoid long dead times between pulses. A preferred laser system which meets these requirements is the Nd:YAG pumped dyelaser. Using dye lasers, it is possible to achieve 20 mJ of energy in the visible. With further mixing and frequency doubling provided in laser system 22, the system can provide between one and ten mJ over the UV (from 220 nanometers).

Figure 4:
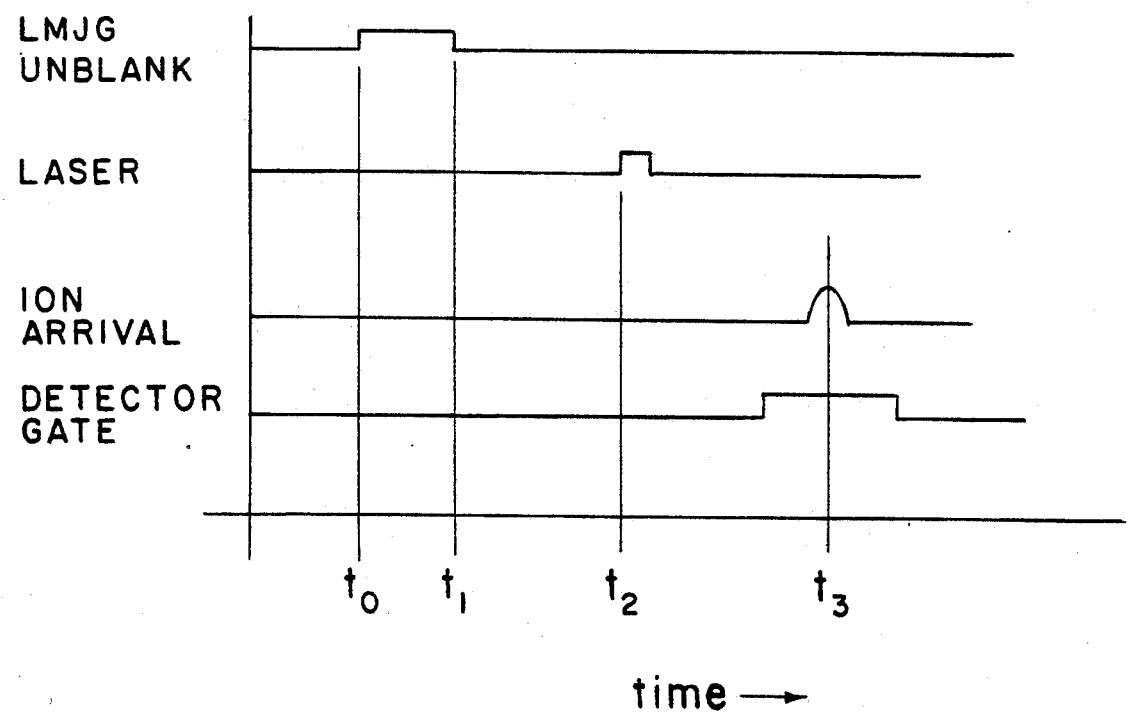
FIG. 4 is a timing diagram illustrating the time-relationships of certain signals experienced in the system of FIG. 1.

Referring back to FIG. 1, the system's operation will be described in conjunction with the timing diagrams shown in FIG. 4. At time t0, an unblanking signal is applied to LMIG 14 by processor 20, thereby enabling a pulse of ions to be directed at substrate 10. During the time t0-t1 ion beam 16 is focused onto the surface of the sample on substrate 10 and causes particles to be emitted therefrom. At t1, ion beam 16 is blanked. Subsequently at t2, laser system 22 is gated on by processor 20 thereby causing the generation of beam 24 through the particulate cloud above substrate 10 created through the action of unblanked ion beam 16. The delay in gating laser system on until t2 enables the particles which are desorbed from the surface of the sample to travel to the region of beam 24. The interaction between beam 24 and the particulate cloud results in a multiphoton resonant ionization of neutral particles in the cloud, thereby increasing the ionized particles available for detection.

The ionized species from the sample are accelerated by plates 36 into a reflector 28 which then directs the species to microchannel platedetector 29. Just prior to the expected time of arrival of the species at multichannel plates/detector 29, a gating pulse may (but is not required) be applied via line 32 to enable the detection function. When the ions impact upon multichannel plate and they create a signal that is passed through AD converter 31 and conductor 33 to processor 20.

Within processor 20, the commencement of the laser pulse causes a teiming function to begin that enables the mass of the ionized particles reaching detector 29 to be determined. In addition, processor 20, through appropriate timing controls (not shown) applies both a raster scan signal to display 30 and to LMIG 14 to enable the synchronization of the raster scan of display 30 with that of the scan of beam 16 from LMIG 14. In such manner, processor 20 processes outputs from detector 29 and supplies image signals to display 30 so as to enable display of a raster scan view of the surface of substrate 10. Processor 20, using known mass spectrometry procedures can, by determining the time-of-flight of the ionic species to detector 29 determine the mass of the species. By appropriate selection of flight times, processor 20 is thereby able to selectively provide to display 30 only those species of interest.

As above indicated, the system of FIG. 1 is particularly useful in imaging biological materials. For instance, Lerner and Benkovic have developed a means for generating a large combinatorial library of the immune globulin repertoire in phage lambda. The net result of their procedure is a library containing some one million clones expressed as phage plaques with a density of approximately 30,000 plaques per plate. Those plaques can be transferred to nitrocellulose filter disks and the disks screened with radioactive antigen for antigen-antibody binding. Each positive colony then is a potential catalytic antibody.

A major problem is how to screen the replica plates directly for the production of small quantities of molecular products derived from a catalytic process. The high spatial resolution of the system of FIG. 1, along with the extremely sensitive detection limits of multi photon resonance imaging detection, offers a unique means for sensitivity screening of catalytic antibodies directly on the nitrocellulose replica filters. The plaques on the nitrocellulose filters contain approximately $10^8$ molecules. This concentration will allow qualitative detection of the desorbed molecular ion (or representative fragment ions) given the sensitivity and selectivity of the system of FIG. 1.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

We claim:

1. A system for enabling quantitative analysis and imaging of specific chemical species on a surface of a sample, said system comprising:

a liquid metal ion source for directing a tightly focused beam of ions at said sample, said beam having an ion density that does not materially change surface properties of the sample;

control means connected to said liquid metal ion source for gating on said ion beam for a period of time sufficient to enable said liquid metal ion source to achieve said tight focus of said ion beam at the sample and for further scanning said ion beam across said sample;

a laser beam positioned over said sample and exhibiting a wavelength that effectively ionizes components of said sample that are liberated therefrom by action of said scanned ion beam, said laser beam being unfocussed within a region occupied by said components of said sample;

detector means for providing indications to said control means of detected ions created by action of said laser beam on said sample components; and display means connected to said control means for producing an image of said sample surface in accordance with outputs from said detector means.

2. The system as recited in claim 1 wherein said control means periodically gates on said laser means and further determines the mass of said detected ions by use of a timing signal function that is determined from the gating of said laser means.

3. The system as recited in claim 2 wherein said liquid metal ion source includes an aperture and electrostatic plates for controlling said ion beam position with respect to said aperture, said control means emplacing a gating potential on said electrostatic plates to position said beam centrally in said aperture, said gating potential having a time duration that is sufficiently long to enable said beam to stabilize in said aperture.

4. The system as recited in claim 3 wherein said beam is focused to diameter that is less than one micron.

5. The system as recited in claim 3 wherein said beam is gated on for at least 100 nanoseconds.

6. The system as recited in claim 1 wherein said sample is insulating in character, said sample tending to attain positive charges from said ion beam, said system further comprising:

electron source means operated by said control means during a period when said ion beam is not gated on, whereby electrons from said electron source tend to neutralize said positive charges.

* * * * *